United States Patent
Woodward et al.

(10) Patent No.: US 10,463,261 B2
(45) Date of Patent: Nov. 5, 2019

(54) AUTOMATIC ESTIMATION OF PULSE DEFICIT

(71) Applicant: Covidien LP, Mansfield, MA (US)

(72) Inventors: Jonathan James Woodward, Annapolis, MD (US); Dietrich Otto Ruehlmann, Gaithersburg, MD (US); David Benjamin Berlin, Niwot, CO (US); Daniel Wayne Bartlett, Annapolis, MD (US)

(73) Assignee: Covidien LP, Bolder, CO (US)

( * ) Notice: Subject to any disclaimer, the term of this patent is extended or adjusted under 35 U.S.C. 154(b) by 398 days.

(21) Appl. No.: 15/244,812

(22) Filed: Aug. 23, 2016

(65) Prior Publication Data
US 2018/0055382 A1  Mar. 1, 2018

(51) Int. Cl.
| A61B 5/0245 | (2006.01) |
|---|---|
| A61B 5/0402 | (2006.01) |
| A61B 5/0205 | (2006.01) |
| A61B 5/00 | (2006.01) |
| A61B 5/024 | (2006.01) |

(52) U.S. Cl.
CPC ......... *A61B 5/0245* (2013.01); *A61B 5/0024* (2013.01); *A61B 5/0205* (2013.01); *A61B 5/02416* (2013.01); *A61B 5/02438* (2013.01); *A61B 5/02455* (2013.01); *A61B 5/0402* (2013.01); *A61B 5/7246* (2013.01); *A61B 5/6833* (2013.01); *A61B 5/746* (2013.01)

(58) Field of Classification Search
CPC ... A61B 5/0245; A61B 5/0024; A61B 5/0205; A61B 5/02416; A61B 5/02438; A61B 5/02455; A61B 5/0402; A61B 5/7246; A61B 5/6833; A61B 5/746
USPC ................................. 600/481, 483, 500–503
See application file for complete search history.

(56) References Cited

U.S. PATENT DOCUMENTS

| 5,123,420 A * | 6/1992 | Paret ................... A61B 5/02411 |
|---|---|---|
| | | 600/509 |
| 6,178,343 B1 * | 1/2001 | Bindszus .............. A61B 5/0245 |
| | | 600/323 |
| 6,304,773 B1 * | 10/2001 | Taylor ....................... A61N 1/39 |
| | | 600/515 |
| 6,440,082 B1 * | 8/2002 | Joo ....................... A61B 5/0535 |
| | | 600/483 |
| 6,553,251 B1 * | 4/2003 | Lahdesmaki ........ A61B 5/0006 |
| | | 600/519 |
| 6,893,396 B2 * | 5/2005 | Schulze ............... A61B 5/0022 |
| | | 600/300 |
| 7,488,293 B2 * | 2/2009 | Marcovecchio ......... A61N 1/39 |
| | | 600/484 |

(Continued)

*Primary Examiner* — Navin Natnithithadha
(74) *Attorney, Agent, or Firm* — Holland & Hart LLP

(57) ABSTRACT

Methods, systems, and devices for determining pulseless electrical activity (PEA) are described. The method may include determining by using a first sensor on a person, a heart rate of the person based on sensed electrical activity of the person. A pulse rate of the person may be determined using a second sensor, the pulse rate of the person being based on at least one sensed parameter other than the sensed electrical activity. The method may then include determining a correlation of the determined heart rate and the determined pulse rate and then generating an alert event based at least in part on the correlation being outside of a predetermined threshold.

16 Claims, 14 Drawing Sheets

(56) References Cited

U.S. PATENT DOCUMENTS

| | | | | |
|---|---|---|---|---|
| 8,092,392 B2* | 1/2012 | Stickney | A61B 5/0809 | 600/500 |
| 8,135,462 B2* | 3/2012 | Owen | A61B 5/02416 | 600/310 |
| RE44,187 E* | 4/2013 | Marcovecchio | A61N 1/39 | 600/484 |
| 8,506,480 B2* | 8/2013 | Banet | G16H 40/67 | 600/301 |
| 8,591,425 B2* | 11/2013 | Owen | A61B 5/02416 | 600/500 |
| 8,663,121 B2* | 3/2014 | Stickney | A61B 5/0809 | 600/508 |
| 8,738,118 B2* | 5/2014 | Moon | A61B 5/0002 | 600/513 |
| 8,870,797 B2* | 10/2014 | Paradis | A61H 31/005 | 600/508 |
| 8,992,432 B2* | 3/2015 | Owen | A61B 5/02416 | 600/481 |
| 9,216,001 B2* | 12/2015 | Owen | A61B 5/02416 | |
| 9,248,306 B2* | 2/2016 | Joo | A61N 1/3987 | |
| RE45,922 E* | 3/2016 | Marcovecchio | A61N 1/39 | |
| 9,585,563 B2* | 3/2017 | Mensinger | A61B 5/0004 | |
| 9,629,566 B2* | 4/2017 | Gilham | A61B 5/7246 | |
| 9,950,178 B2* | 4/2018 | Stickney | A61B 5/0809 | |
| 9,981,142 B2* | 5/2018 | Joo | A61N 1/3987 | |
| 2002/0082491 A1* | 6/2002 | Nissila | A61B 5/024 | 600/391 |
| 2003/0109790 A1* | 6/2003 | Stickney | A61B 5/0809 | 600/500 |
| 2004/0116969 A1* | 6/2004 | Owen | A61B 5/02416 | 607/6 |
| 2004/0215244 A1* | 10/2004 | Marcovecchio | A61N 1/39 | 607/5 |
| 2005/0043763 A1* | 2/2005 | Marcovecchio | A61N 1/39 | 607/5 |
| 2005/0256415 A1* | 11/2005 | Tan | A61B 5/0464 | 600/509 |
| 2006/0009809 A1* | 1/2006 | Marcovecchio | A61N 1/39 | 607/5 |
| 2006/0247549 A1* | 11/2006 | Chan | A61B 5/0006 | 600/519 |
| 2007/0288060 A1* | 12/2007 | Stickney | A61B 5/0809 | 607/8 |
| 2008/0150731 A1* | 6/2008 | Laukkanen | A61B 5/1118 | 340/573.1 |
| 2008/0208273 A1* | 8/2008 | Owen | A61B 5/02416 | 607/6 |
| 2009/0131224 A1* | 5/2009 | Yuen | A61B 5/0002 | 482/3 |
| 2010/0114219 A1* | 5/2010 | Stickney | A61B 5/0809 | 607/5 |
| 2010/0114220 A1* | 5/2010 | Paradis | A61H 31/005 | 607/6 |
| 2010/0121208 A1* | 5/2010 | Stickney | A61B 5/0809 | 600/500 |
| 2010/0121392 A1* | 5/2010 | Stickney | A61B 5/0809 | 607/5 |
| 2010/0160796 A1* | 6/2010 | Banet | A61B 5/02125 | 600/485 |
| 2010/0268518 A1* | 10/2010 | Sugo | A61B 5/0285 | 703/2 |
| 2010/0292748 A9* | 11/2010 | Stickney | A61B 5/0809 | 607/8 |
| 2011/0066009 A1* | 3/2011 | Moon | A61B 5/0002 | 600/301 |
| 2011/0066010 A1* | 3/2011 | Moon | A61B 5/0205 | 600/301 |
| 2011/0066044 A1* | 3/2011 | Moon | A61B 5/021 | 600/485 |
| 2011/0066045 A1* | 3/2011 | Moon | A61B 5/021 | 600/485 |
| 2011/0066050 A1* | 3/2011 | Moon | A61B 5/0006 | 600/509 |
| 2011/0066051 A1* | 3/2011 | Moon | A61B 5/0002 | 600/509 |
| 2012/0029368 A1* | 2/2012 | Joo | A61B 5/0535 | 600/500 |
| 2012/0035485 A1* | 2/2012 | Owen | A61B 5/02416 | 600/479 |
| 2012/0035676 A1* | 2/2012 | Owen | A61B 5/02416 | 607/6 |
| 2012/0302896 A1* | 11/2012 | Joo | A61B 5/0535 | 600/479 |
| 2013/0060148 A1* | 3/2013 | Owen | A61B 5/02416 | 600/479 |
| 2013/0338724 A1* | 12/2013 | Joo | A61N 1/3987 | 607/3 |
| 2014/0058469 A1* | 2/2014 | Owen | A61B 5/02416 | 607/6 |
| 2014/0184422 A1* | 7/2014 | Mensinger | A61B 5/0004 | 340/870.02 |
| 2014/0249431 A1* | 9/2014 | Banet | A61B 5/01 | 600/485 |
| 2014/0266939 A1* | 9/2014 | Baringer | H01Q 21/28 | 343/729 |
| 2014/0275852 A1* | 9/2014 | Hong | A61B 5/02427 | 600/301 |
| 2015/0173689 A1* | 6/2015 | Owen | A61B 5/02416 | 600/454 |
| 2015/0366469 A1* | 12/2015 | Harris | A61B 5/0245 | 600/301 |
| 2016/0067499 A1* | 3/2016 | Owen | A61B 5/02416 | 600/324 |
| 2016/0106992 A1* | 4/2016 | Joo | A61N 1/3987 | 600/484 |
| 2018/0028830 A9* | 2/2018 | Joo | A61N 1/3987 | |

* cited by examiner

AUTOMATIC ESTIMATION OF PULSE DEFICIT

BACKGROUND

The following relates generally to determining a heart rate, and more specifically to automatic estimation of pulse deficit.

In a healthcare facility such as a hospital, physiological parameters of the patient (e.g., heart rate, respiratory rate, blood pressure) may be monitored by one or more medical devices. The medical devices may be battery powered and may wirelessly transmit measured patient data over a wireless network within the hospital, thereby allowing the patient to move freely through the hospital while being monitored. Clinicians may remotely monitor the patient by accessing the patient data at a central nurse station or on any web enabled device connected to the network (e.g., smartphone or tablet).

Various physiological parameters may be monitored. A typical monitored physiological parameter is a patient's heart rate. However, monitoring of a heart rate alone may not be sufficient to detect a clinical condition known as pulseless electrical activity (PEA). PEA is a clinical condition of cardiac arrest characterized by cardiac electrical activity that shows an observable heart rhythm that would normally be accompanied by a mechanical pulse of the heart, but where no pulse is actually generated. Under normal circumstances, electrical activation of muscle cells precedes mechanical contractions of the heart. During PEA, however, electrical activity is observed, but the heart either does not contract or contractions are insufficient to generate a pulse and supply blood to a person's organs. In other words, in a person susceptible to PEA, cardiac mechanical activity may not necessarily follow cardiac electrical activity. PEA may lead to a loss of cardiac output. As a result, blood supply to various organs, including to the brain, may be interrupted. Consequently, a person may lose consciousness and/or stop breathing, which may sometimes be the first observable signs that a person is suffering from PEA.

Relying on a person to lose consciousness or stop breathing is not an ideal method to discover that a person is suffering from PEA. Nevertheless, constant observation by a medical professional or caretaker may not be feasible. Therefore, improvements in monitoring and detecting PEA are desired.

SUMMARY

The described features generally relate to methods, systems, devices, or apparatuses that support automatic estimation of pulse deficit. For example, an apparatus may be a wearable physiological sensing device that may determine, by using a first sensor on a person, a heart rate of the person based on sensed electrical activity of the person. The apparatus may also determine, by using a second sensor on the person, a pulse rate of the person based on at least one sensed parameter other than the sensed electrical activity of the person. The heart rate and the pulse rate may be correlated. The correlation may include comparing a timing of the heart rate and the pulse rate. Alternatively, the correlation may include a comparing of the frequency domain analysis of the heart rate and the pulse rate. The correlation may occur over one or more predetermined time periods. As a result of the correlation, the apparatus may generate an alert event. The alert event may be based at least in part on the correlation being outside of a predetermined threshold. The alert event may also be transmitted to a device apart from the sensing apparatus.

A method of determining a heart rate is described. The method may include determining, using at least a first sensor on a person, a heart rate of the person based on sensed electrical activity of the person, determining, using at least a second sensor on the person, a pulse rate of the person based on at least one sensed parameter other than the sensed electrical activity of the person, determining a correlation of the determined heart rate and the determined pulse rate, and generating an alert event based at least in part on the correlation being outside of a predetermined threshold.

An apparatus for determining a heart rate is described. The apparatus may include a processor, memory in electronic communication with the processor, and instructions stored in the memory. The instructions may be operable to cause the processor to determine, using at least a first sensor on a person, a heart rate of the person based on sensed electrical activity of the person, determine, using at least a second sensor on the person, a pulse rate of the person based on at least one sensed parameter other than the sensed electrical activity of the person, determine a correlation of the determined heart rate and the determined pulse rate, and generate an alert event based at least in part on the correlation being outside of a predetermined threshold.

A device for determining a heart rate is described. The apparatus may include means for determining, using at least a first sensor on a person, a heart rate of the person based on sensed electrical activity of the person, means for determining, using at least a second sensor on the person, a pulse rate of the person based on at least one sensed parameter other than the sensed electrical activity of the person, means for determining a correlation of the determined heart rate and the determined pulse rate, and means for generating an alert event based at least in part on the correlation being outside of a predetermined threshold.

In some examples of the method, device, and apparatus described above, determining the correlation may include comparing a timing of the determined heart rate and the determined pulse rate. In some examples of the method, device, and apparatus described above, determining the correlation may include comparing a frequency domain analysis of the determined heart rate and the determined pulse rate.

In some examples of the method, device, and apparatus described above, the alert event indicates a Pulseless Electrical Activity (PEA) condition. In some examples, the sensed electrical activity of the person is an electrocardiogram (ECG) of the person. In some examples, the at least one sensed parameter is based on an arterial blood pressure of the person.

In some examples of the method, device, and apparatus described above, the predetermined threshold may include a first predetermined threshold and a second predetermined threshold. Additionally, generating the alert event may include generating a first category of alert event when the correlation is between the first predetermined threshold and the second predetermined threshold and generating a second category of alert event when the correlation is outside of both the first predetermined threshold and the second predetermined threshold.

In some examples of the method, device, and apparatus described above, determining the correlation includes determining the correlation over a period of time where multiple periods of the person's heart rate and pulse rate are determined. In some examples, the method, device, or apparatus described above may additionally include remotely updating the predetermined threshold. In some examples, the method, device, or apparatus described above may additionally include transmitting the alert event to a central station via a network. In some examples, the method, device, or apparatus described above may additionally include storing the alert event for later transmission if the network is not available for transmission.

In some examples, the method, device, or apparatus described above may additionally include transmitting, with the alert event, the determined heart rate and the determined pulse rate. In some examples, the method, device, or apparatus described above may additionally include determining the pulse rate comprises: obtaining a sensed parameter via an accelerometer, oximeter, or an optical pulse rate monitor.

In some examples of the method, device, and apparatus described above, the correlation may occur on a device configured for use with the at least first sensor and the at least second sensor. In some examples, the method, device, or apparatus described above may additionally include transmitting the determined heart rate and the determined pulse rate of the person to a central station via a network, wherein the correlation occurs at the central station.

DETAILED DESCRIPTION

Figure 1:
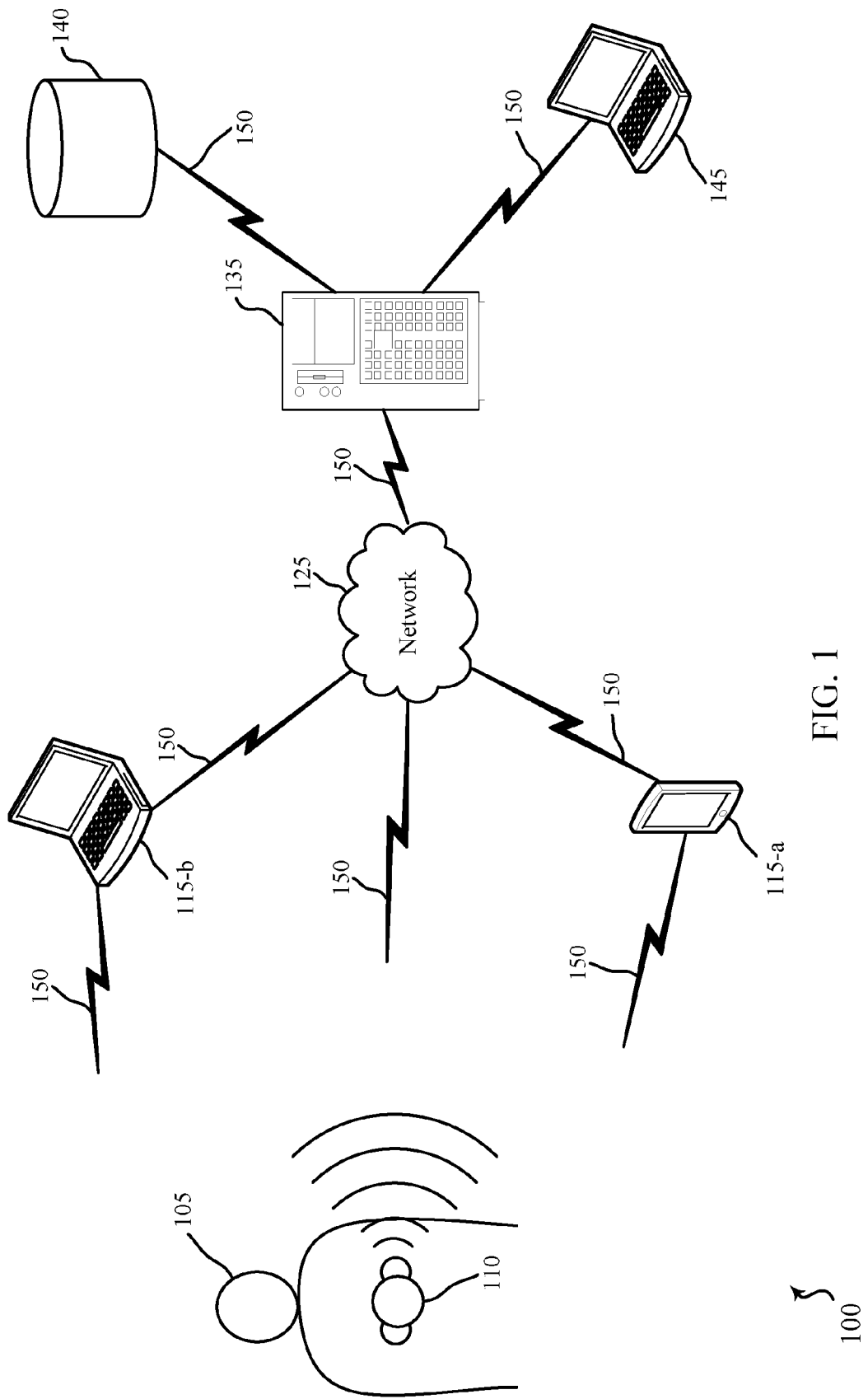
FIG. 1 illustrates an example of a system for wireless communication that supports automatic estimation of pulse deficit in accordance with aspects of the present disclosure.

Pulseless electrical activity (PEA) is not uncommon. According to some estimates, PEA may occur in as many as 20% of cardiac arrests suffered by individuals outside of a hospital in the United States. PEA also occurs in patients already admitted to hospitals. In cardiac arrest situations, patient outcomes may significantly improve if PEA may be identified and treated quickly and appropriately. A major factor that may influence PEA outcomes is a health provider's ability to accurately assess the presence or absence of a pulse during an assessment of a patient. However, a PEA condition may be readily missed during diagnosis if a patient's cardiac activity is solely monitored using an electrocardiogram (ECG), which is commonly the case for in-hospital monitored patients. The presence of an organized and regular cardiac rhythm in an ECG may lead clinicians to believe that the patient is in a stable condition despite a lack of mechanical contraction.

Another misdiagnosis may occur if a medical provider recognizes an ECG rhythm but is unable to locate a pulse on the patient, even though one is really present. As a result, the provider might incorrectly determine the presence of PEA and proceed with treatment despite the presence of a pulse. Given the potential for various outcomes and influencing factors, it is crucial for emergency medical service (EMS) providers to have tools at their disposal to accurately diagnose PEA.

Currently deployed pulse rate monitors may be dedicated "spot check" systems that are used on a patient for a few minutes each day. As a result the number of pulse rate measurements that are available for analysis during any given day may be significantly limited. Other systems may be used which collect both ECG and pulse rate information concurrently. However, these systems lack analysis features that use both ECG and pulse rate information for the purposes of determining PEA. Thus it may be beneficial to provide a wearable physiological sensing device having, for example, a first sensor to determine a heart rate of a person, and a second sensor to determine a pulse rate of the person, and which may analyze the determined heart rate and pulse rate to assess a PEA condition. The device may include components which may determine a correlation of the determined heart rate and the determined pulse rate and then generate an alert event based in part on the correlation being outside of a predetermined threshold. Accuracy and timeliness of PEA diagnosis may thus be achieved by use of the device.

Aspects of the disclosure are initially described in the context of a wireless patient monitoring system. Specific examples are described for determining a heart rate and a pulse rate of a person, determining a correlation between the two, and then generating an alert event based in part on the correlation being outside of a predetermined threshold. Aspects of the disclosure are further illustrated by and described with reference to apparatus diagrams, system diagrams, and flowcharts that relate to automatic estimation of pulse deficit.

FIG. 1 illustrates an example of a wireless patient monitoring system 100 in accordance with various embodiments of the present disclosure. The wireless patient monitoring system 100 may include a patient 105 wearing, carrying, or otherwise coupled with a medical device 110. Although a single medical device 110 is shown, multiple medical devices 110 may be coupled to the patient 105. The patient 105 may be a patient in a hospital, nursing home, home care, a medical facility, or another care facility. The medical device 110 may transmit signals via wireless communications links 150 to computing devices 115 or to a network 125.

The medical device 110 may include one or more sensors configured to collect a variety of physiological parameters as well as information related to the location and movement of the patient 105. For example, the medical device 110 may include a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, a sensor which triangulates position from multiple local computing devices 115, or any other sensor configured to collect physiological, location, or motion data associated with the patient 105.

The medical device 110 may be coupled with the patient 105 in a variety of ways depending on the data being collected. For example, the medical device 110 may be directly coupled with the patient 105 (e.g., physically connected to the patient's chest, worn around the patient's wrist, attached to the patient's finger, or positioned over the patients nose or mouth). The data collected by the medical device 110 may be wirelessly transmitted to either the computing devices 115 or to the remote computing device 145 (via the network 125 and central station 135). Data transmission may occur via, for example, frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (Wi-MAX), etc.).

Computing device 115-a may be a wireless device such as a tablet, cellular phone, personal digital assistant (PDA), a dedicated receiver, or other similar device or a spatially distributed network of devices configured to receive signals from the medical device 110. Computing device 115-b may be a wireless laptop computer, a clinician Workstation on Wheels, or a smart hospital bed configured to receive signals from the medical device 110. The computing devices 115 may be in communication with a central station 135 via network 125.

The medical device 110 may also communicate directly with the central station 135 via the network 125. The central station 135 may be a server or a central nurse station located within the hospital or in a remote location. The central station 135 may be in further communication with one or more remote computing devices 145, thereby allowing a clinician to remotely monitor the patient 105. Remote computing device 145 may receive various alerts from central station 135. The central station 135 may also be in communication with various remote databases 140 where the collected patient data may be stored. In some cases, the remote databases 140 include electronic medical records (EMR) applications for storing and sharing patient data.

The medical device 110 may be configured to trigger or sound an alert based on certain criteria associated with the patient. In some cases, the alert is generated at the medical device 110 within the room of the patient 105. Additionally or alternatively, the medical device 110 may trigger an alert to be sent to a remote location (e.g., central station 135, remote computing devices 145, etc.). The medical device 110 may monitor physiological parameters of the patient such as heart rate, pulse rate, blood pressure, etc., and may trigger an alert when the measured physiological parameter(s) crosses a threshold. The alert may also be triggered if a correlation between two or more of the parameters is outside a predetermined threshold. The alert may indicate a PEA condition.

In accordance with various embodiments, methods and apparatuses are described for determining a heart rate and a pulse rate using one or more sensors on a person. These sensors may be located in medical device 110. In accordance with some embodiments, methods and apparatuses are described for determining a correlation of the determined heart rate and pulse rate. This correlation may occur at medical device 110, central station 135, or remote computing device 145.

Figure 2:
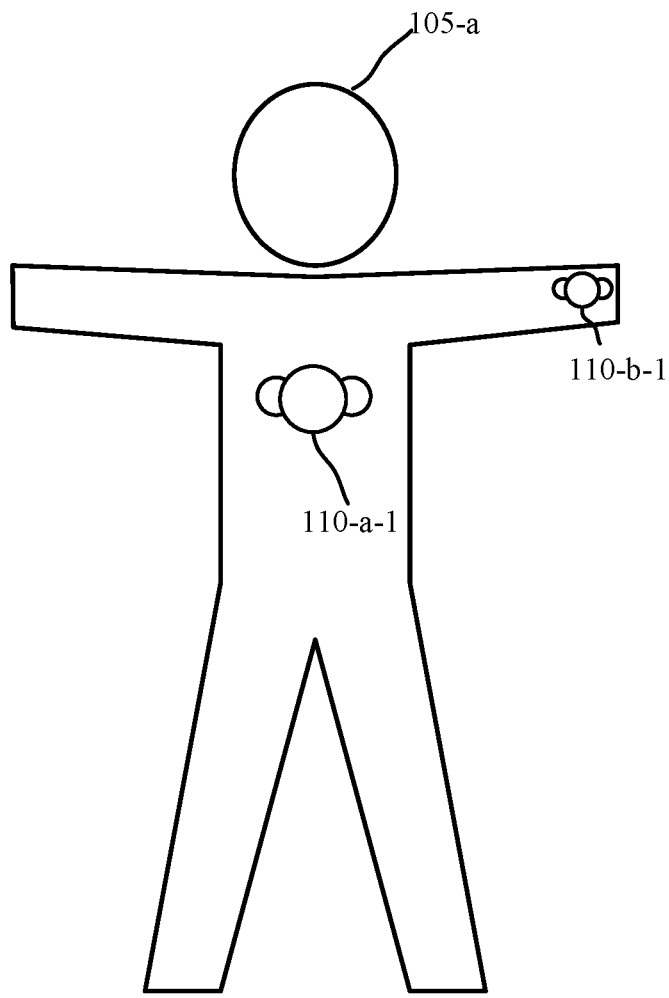
FIG. 2 illustrates an example system for automatic estimation of pulse deficit in accordance with aspects of the present disclosure.

FIG. 2 illustrates an example of a system 200 for automatic estimation of pulse deficit. In some cases, system 200 may be include, as aspects of the system 200, examples of one or more medical devices 110 illustrated in FIG. 1. System 200 may include a patient 105-a wearing a medical device 110-a-1 and medical device 110-b-1.

The medical device 110-a-1 may be an example of a device that senses an electrical activity of patient 105-a, such as a heart rate. Medical device 110-a-1 may be a diagnostic tool that is routinely used to assess the electrical and muscular functions of the heart, and may generate an ECG. Medical device 110-a-1 may have one or more electrodes that may be placed on the body of patient 105. Medical device 110-a-1 may receive signals from each electrode and may record, process, and/or transmit the signals. Correlations between one or more physiological measurements may occur at medical device 110-a-1.

The medical device 110-b-1 may be an example of a device that determines a pulse rate of patient 105-a. To do so, medical device 110-b-1 may sense one or more physiological parameters from which pulse rate may be determined. For example, medical device 110-b-1 may sense an arterial blood pressure of patient 105-a. Alternatively, medical device 110-b-1 may attach to a fingertip and may monitor the amount of oxygen carried in the bloodstream of patient 105-a. Medical device 110-b-1 may use an accelerometer to pulse rate-related movement. Using the measured parameters, medical device 110-b-1 may determine a pulse rate. Medical device 110-b-1 may receive signals and may record, process, and/or transmit the signals. Correlations between one or more physiological measurements may occur at medical device 110-b-1.

Medical device 110-a-1 and medical device 110-b-1 may communicate with each other. For example, medical device 110-a-1 may detect a heart rate for patient 105-a and may transmit the detected heart rate to medical device 110-b-1. Alternatively, medical device 110-b-1 may detect a pulse rate for patient 105-a and may transmit the detected pulse rate to medical device 110-a-1. In yet another alternative, medical device 110-a-1, 110-b-1 may transmit sensed data without first determining from the sensed data a heart rate or a pulse rate. In this circumstance, the medical device 110-a-1, 110-b-1 which receives the transmitted data may determine a relevant physiological parameter from the sensed data. The medical device 110-a-1, 110-b-1 that is in possession of both a detected heart rate and a detected pulse rate may correlate the two physiological parameters in order to assess a PEA condition. Alternatively, the detected physiological parameters may be transmitted to another device for correlation in order to assess a PEA condition.

Figure 3:
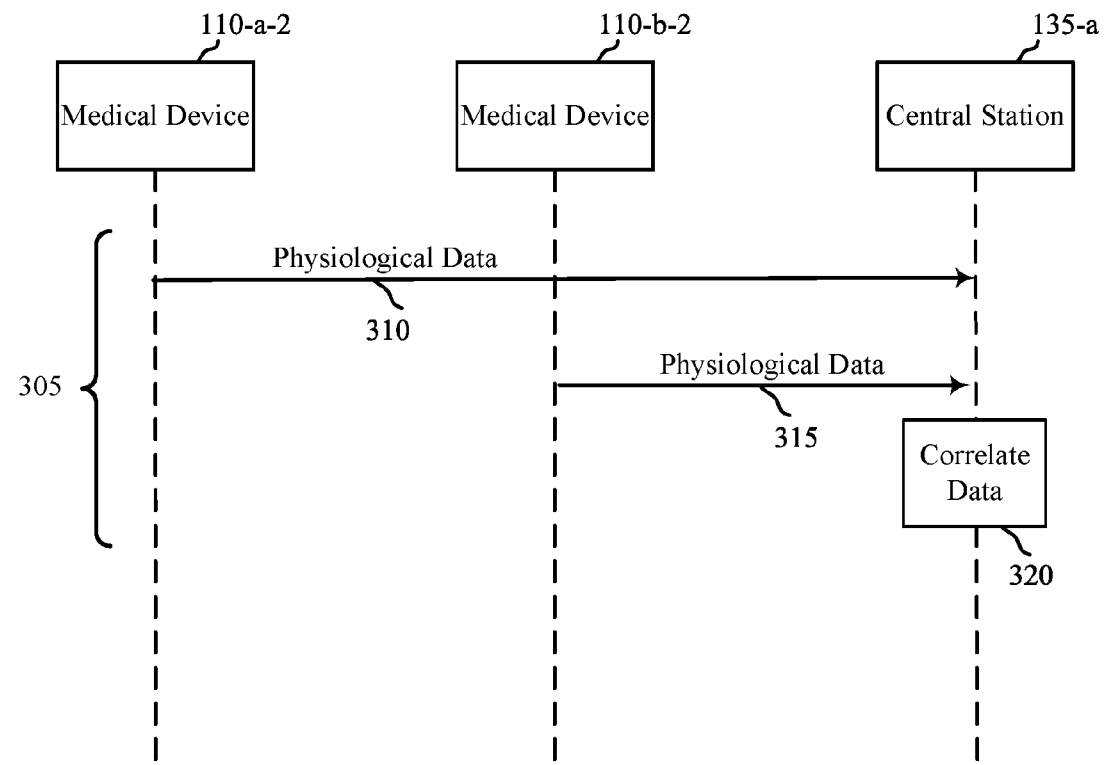
FIGS. 3 through 5 illustrate flow diagrams for automatic estimation of pulse deficit in accordance with aspects of the present disclosure.
Figure 4:
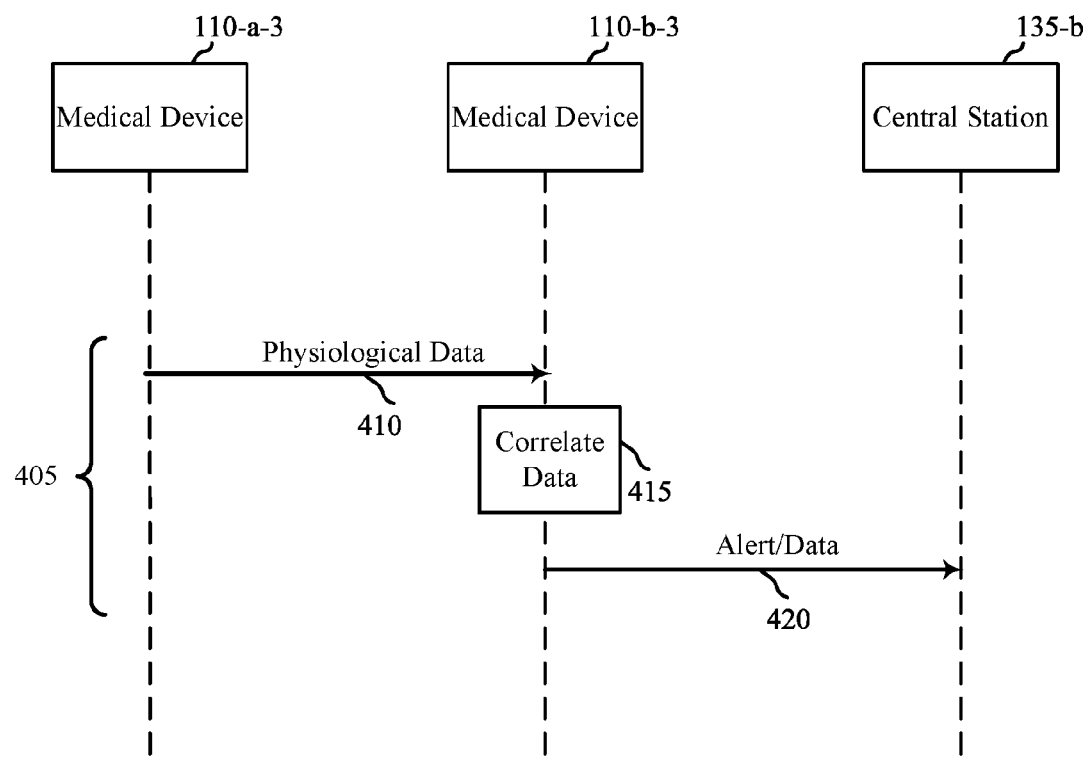
Figure 5:
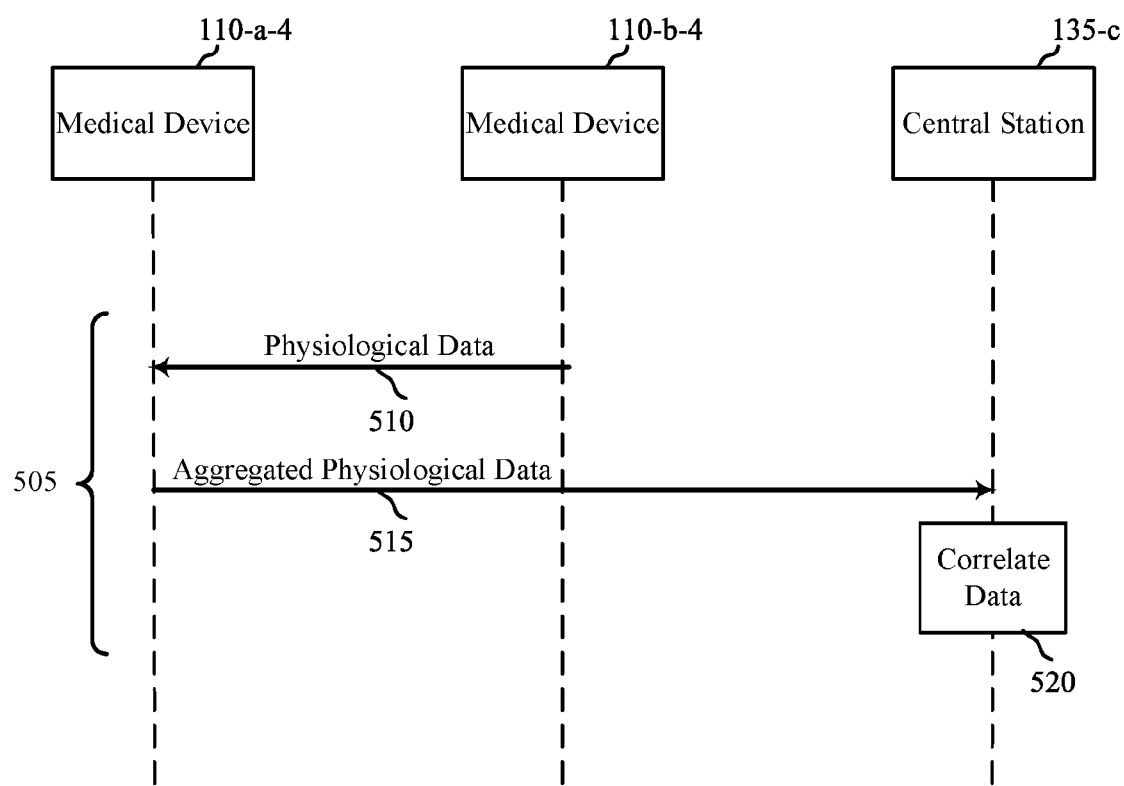

FIGS. 3, 4, and 5 show example flow diagrams 300, 400, 500 for automatic estimation of pulse deficit. In some cases, flow diagrams 300, 400, 500 may represent aspects of techniques performed by a medical device 115 or a central station 135 as described with reference to FIGS. 1 and 2. Medical device 110-a-2 may be similar to medical device 110-a-1 described in FIG. 2 and medical device 110-b-2 may be similar to medical device 110-b-1 described in FIG. 2.

Medical devices 110, 110, and central station 135 may perform various techniques 305, 405, and 505, as illustrated in FIGS. 3, 4, and 5, in performing automatic estimation of pulse deficit. FIG. 3 illustrates technique 305. In technique 305, medical devices 110-a-2 and 110-b-2 may send physiological data 310 and 315, respectively to central station 135-a. Medical device 110-a-2 may send physiological data such as ECG data and medical device 110-b-2 may send physiological data such as pulse rate or oxygen saturation. Central station 135-a may then determine a correlation of the heart rate and the pulse rate. The correlation may include comparing of a timing of the heart rate and a timing of the pulse rate. For example, a measured cycle of electrical activity of a heartbeat may have a corresponding pulse in a subsequent time period. The correlation may also include a comparing of a frequency domain analysis of the heart rate and a frequency domain analysis of the pulse rate. Determining the correlation may occur over a period of time where multiple periods of the person's heart rate and pulse rate are determined.

If the determined correlation is outside of a predetermined threshold, central station 135-*a* may generate an alert which may indicate a PEA condition. The predetermined threshold may also be remotely updated. In some embodiments, the predetermined threshold may be comprised of a first predetermined threshold and a second predetermined threshold where a first category of alert event is generated when the correlation is between the first predetermined threshold and the second predetermined threshold. A second category of alert event may be generated when the correlation is outside of both the first predetermined threshold and the second predetermined threshold. In some embodiments, the alert may be an audible and/or a visible alert at the central station 135-*a*. In other embodiments, the alert may be transmitted to another device, such as to a computing device 115 or a remote computing device 145, as illustrated in FIG. 1. In these cases, the alert may be transmitted with the determined heart rate and the determined pulse rate. The alert may be stored for later transmission if the network is not available for transmission.

In technique 405 of FIG. 4, medical device 110-*a*-3 may transmit its determined physiological data 410 to medical device 110-*b*-3. For example, medical device 110-*a*-3 may transmit an ECG or a determined heart rate to medical device 110-*b*-3. Medical device 110-*b*-3 may correlate the received physiological data 410 with its own determined physiological data at step 415. As an example, medical device 110-*b*-3 may correlate received heart rate data with its own detected pulse rate data. This correlation may be similar to the correlation described in step 320 of FIG. 3. If the determined correlation at step 415 is outside of a predetermined threshold, medical device 110-*b*-3 may transmit an alert event 420 to central station 135-*b*. In addition to the alert event, medical device 110-*b*-3 may transmit the determined physiological data from both medical device 110-*a*-3 and medical device 110-*b*-3. It should be noted that technique 405 may be performed such that medical device 110-*b*-3 first transmits its physiological data to medical device 110-*a*-3, and that the correlation of the data may occur at medical device 110-*a*-3. Medical device 110-*a*-3 is also capable of sending an alert event to central station 135-*b* if the determined correlation is outside of the predetermined threshold.

In technique 505 of FIG. 5, medical device 110-*b*-4 may transmit its determined physiological data 510 to medical device 110-*a*-4. At step 515, medical device 110-*a*-4 may aggregate its own determined physiological data with the physiological data received from medical device 110-*b*-4 and transmit the aggregated data to central station 135-*c*. At step 520, central station 135-*c* may determine a correlation between the received aggregated data 515. This correlation may be similar to the correlation described in steps 320 and 415 of FIGS. 3 and 4. If the determined correlation at step 520 is outside of a predetermined threshold, central station 135-*c* may trigger an alert event. It should be noted that technique 505 may be performed such that medical device 110-*a*-4 first transmits its physiological data to medical device 110-*b*-4, and that the aggregation of the data occurs at medical device 110-*b*-4. Medical device 110-*b*-4 is also capable of transmitting the aggregated data to central station 135-*c*.

Figure 6:
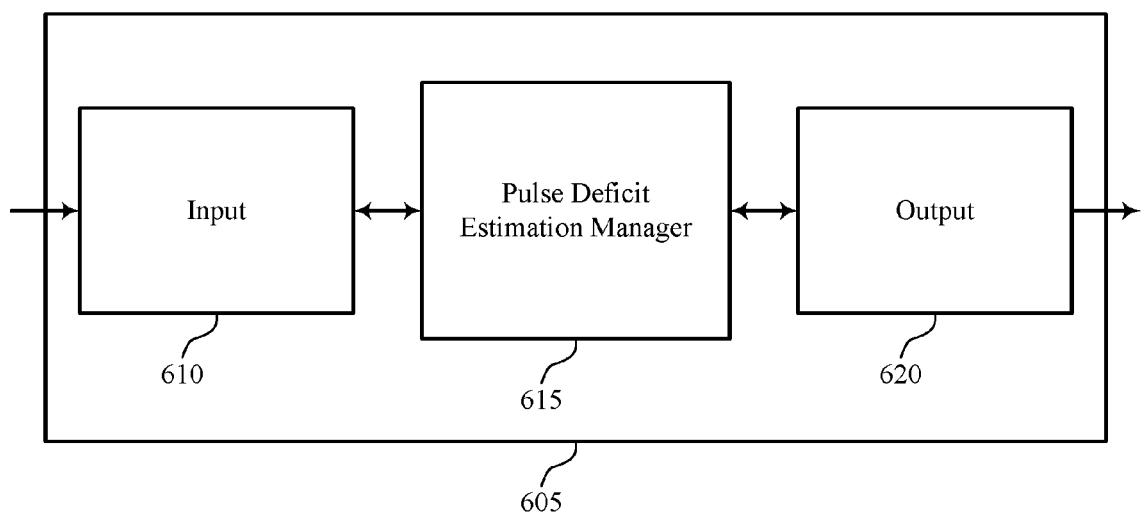
FIGS. 6 through 8 show block diagrams of a device that supports automatic estimation of pulse deficit in accordance with aspects of the present disclosure.

FIG. 6 shows a block diagram 600 of a device 605 that supports automatic estimation of pulse deficit in accordance with various aspects of the present disclosure. Device 605 may be an example of aspects of a medical device 110 as described with reference to FIGS. 1-5. Device 605 may include input 610, pulse deficit estimation manager 615, and output 620. Device 605 may also include a processor. Each of these components may be in communication with one another (e.g., via one or more buses).

Pulse deficit estimation manager 615 may be an example of aspects of the pulse deficit estimation manager 915 described with reference to FIG. 9.

Pulse deficit estimation manager 615 may determine, using at least a first sensor on a person, a heart rate of the person based on sensed electrical activity of the person. Pulse deficit estimation manager 615 may also determine, using at least a second sensor on the person, a pulse rate of the person based on at least one sensed parameter other than the sensed electrical activity of the person. The pulse deficit estimation manager 615 may determine a correlation of the determined heart rate and the determined pulse rate, and generate an alert event based on the correlation being outside of a predetermined threshold.

The first and second sensed parameters may be received by device 605 via input 610. Input 610 may be physically or wirelessly connected to the first and second sensors. For example, device 605 may be an example of medical device 110 (described in FIGS. 1-5) and may receive a first sensed parameter from a sensor that is directly connected to or integrated with the device 605. Device 605 may also receive a second sensed parameter from a different sensor that may be attached to or integrated with a separate medical device. Receipt of this second sensed parameter may be via either a wired connection or a wireless connection.

Output 620 may be used to transmit the sensed parameters to another device, including to a central station 135 (as shown in FIGS. 1, 3, 4, and 5). Alternatively, output 620 may be used to transmit an alert after device 605 has correlated the sensed parameters and determined that a predetermined threshold has been exceeded.

Figure 7:
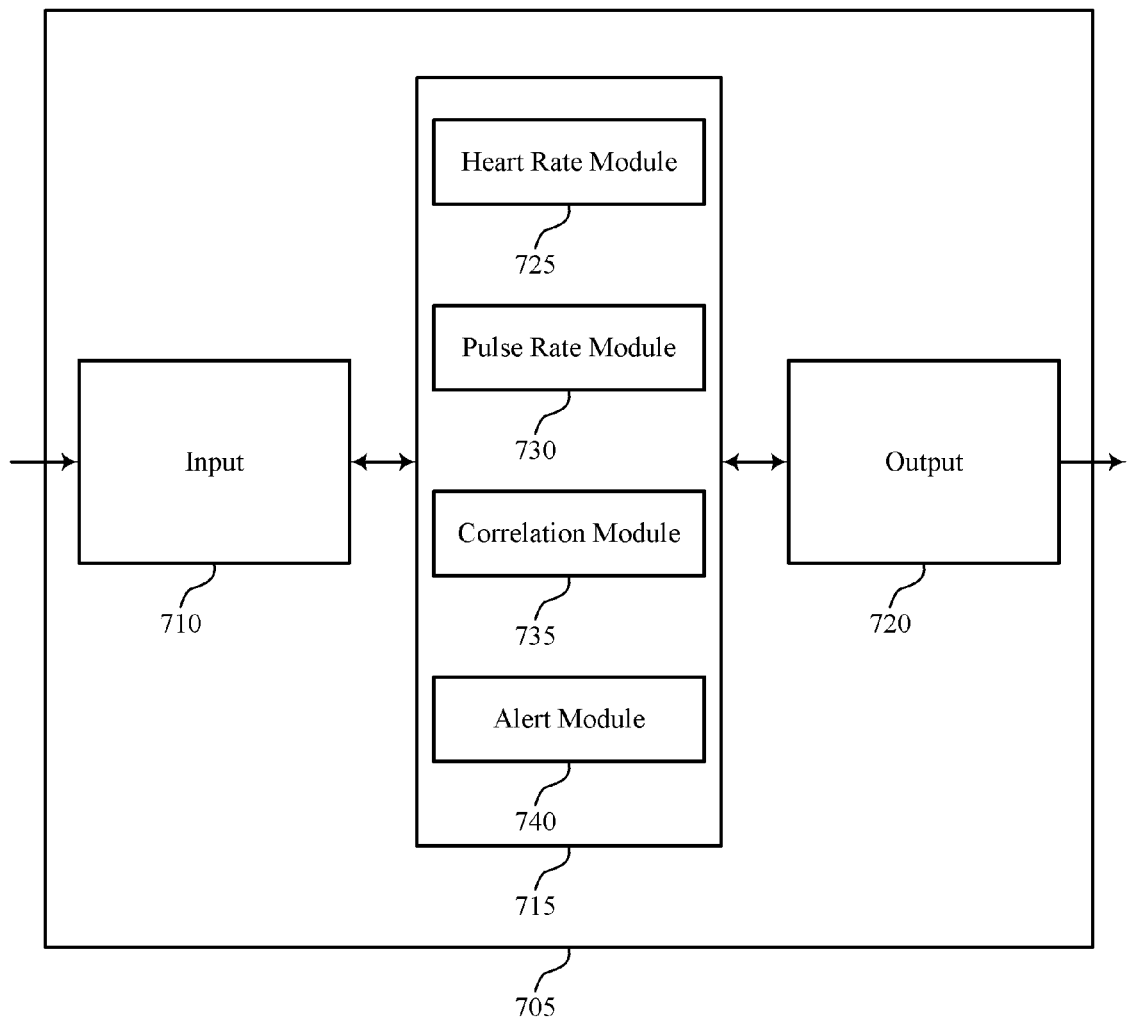

FIG. 7 shows a block diagram 700 of a device 705 that supports automatic estimation of pulse deficit in accordance with various aspects of the present disclosure. Device 705 may be an example of aspects of a device 605 or a medical device 110 as described with reference to FIGS. 1-6. Device 705 may include input 710, pulse deficit estimation manager 715, and output 720. Device 705 may also include a processor. Each of these components may be in communication with one another (e.g., via one or more buses).

Input 710 and output 720 may be examples of input 610 and output 620, respectively, of FIG. 6. Pulse deficit estimation manager 715 may be an example of aspects of the pulse deficit estimation manager 915 described with reference to FIG. 9. Pulse deficit estimation manager 715 may also include heart rate module 725, pulse rate module 730, correlation module 735, and alert module 740.

Heart rate module 725 may determine, using at least a first sensor on a person, a heart rate of the person based on sensed electrical activity of the person. In some cases, the sensed electrical activity of the person is an ECG of the person.

Pulse rate module 730 may determine, using at least a second sensor on the person, a pulse rate of the person based on at least one sensed parameter other than the sensed electrical activity of the person. In some cases, the at least one sensed parameter is based on an arterial blood pressure of the person. In some cases, determining the pulse rate includes: obtaining a sensed parameter via an accelerometer, oximeter, or an optical pulse rate monitor.

Correlation module 735 may determine a correlation of the determined heart rate and the determined pulse rate. In some cases, determining the correlation includes determining the correlation over a period of time where multiple periods of the person's heart rate and pulse rate are determined. In some cases, the correlation occurs on a device configured for use with at least a first sensor and at least a second sensor for sensing physiological parameters from which heart rate and pulse rate may be determined.

Alert module 740 may generate an alert event based on the correlation being outside of a predetermined threshold. In some cases, as explained above, the predetermined threshold may include a first and a second predetermined threshold, with different alert events being generated based on the threshold that has been exceeded. Alert module 740 may transmit the alert event to a central station via a network. Alert module 740 may also store the alert event for later transmission if the network is not available for transmission. In some cases, the alert event indicates a PEA condition.

Figure 8:
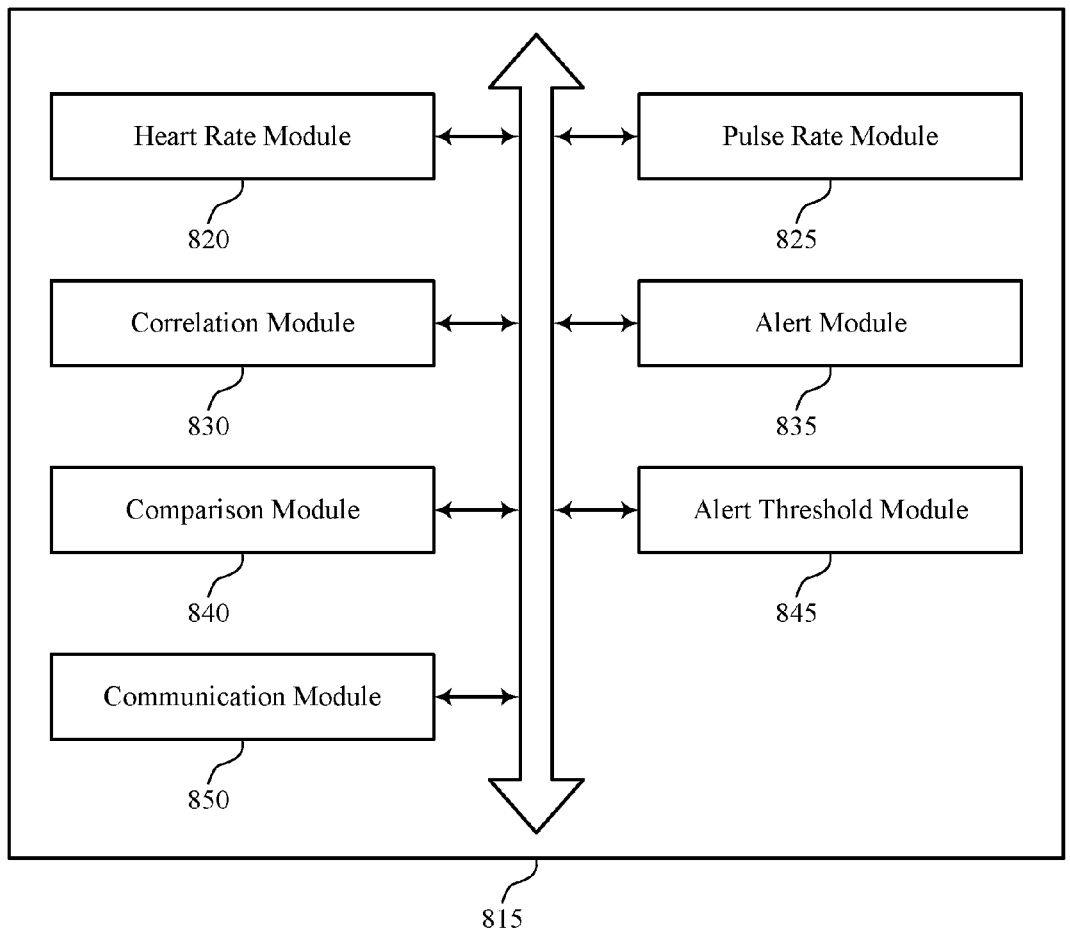

FIG. 8 shows a block diagram 800 of a pulse deficit estimation manager 815 that supports automatic estimation of pulse deficit in accordance with various aspects of the present disclosure. The pulse deficit estimation manager 815 may be an example of aspects of a pulse deficit estimation manager 615, a pulse deficit estimation manager 715, or a pulse deficit estimation manager 915 described with reference to FIGS. 6, 7, and 9. The pulse deficit estimation manager 815 may include heart rate module 820, pulse rate module 825, correlation module 830, alert module 835, comparison module 840, alert threshold module 845, and communication module 850. Each of these modules may communicate, directly or indirectly, with one another (e.g., via one or more buses).

Heart rate module 820 may determine, using at least a first sensor on a person, a heart rate of the person based on sensed electrical activity of the person. In some cases, the sensed electrical activity of the person is an ECG of the person.

Pulse rate module 825 may determine, using at least a second sensor on the person, a pulse rate of the person based on at least one sensed parameter other than the sensed electrical activity of the person. In some cases, the at least one sensed parameter is based on an arterial blood pressure of the person. In some cases, determining the pulse rate includes obtaining a sensed parameter via an accelerometer, oximeter, or an optical pulse rate monitor.

Correlation module 830 may determine a correlation of the determined heart rate and the determined pulse rate. In some cases, determining the correlation includes determining the correlation over a period of time where multiple periods of the person's heart rate and pulse rate are determined. In some cases, the correlation occurs on a device configured for use with at least a first sensor and at least a second sensor.

Alert module 835 may generate an alert event based on the correlation being outside of a predetermined threshold. Alert module 835 may transmit the alert event to a central station via a network. Alert module 835 may also store the alert event for later transmission if the network is not available for transmission. In some cases, the alert event indicates a PEA condition.

Comparison module 840 may compare a timing or frequency analysis of the determined heart rate and the determined pulse rate. In some cases, determining the correlation includes comparing a timing of the determined heart rate and the determined pulse rate. In some cases, determining the correlation includes comparing a frequency domain analysis of the determined heart rate and the determined pulse rate.

Alert threshold module 845 may receive remote instructions to update the predetermined threshold. In some cases, the predetermined threshold comprises a first predetermined threshold and a second predetermined threshold. In some cases, generating the alert event includes generating a first category of alert event when the correlation is between the first predetermined threshold and the second predetermined threshold. In some cases, generating a second category of alert event occurs when the correlation is outside of both the first predetermined threshold and the second predetermined threshold.

Communication module 850 may transmit, with the alert event, the determined heart rate and the determined pulse rate. Communication module 850 may also transmit the determined heart rate and the determined pulse rate of the person to a central station via a network.

Figure 9:
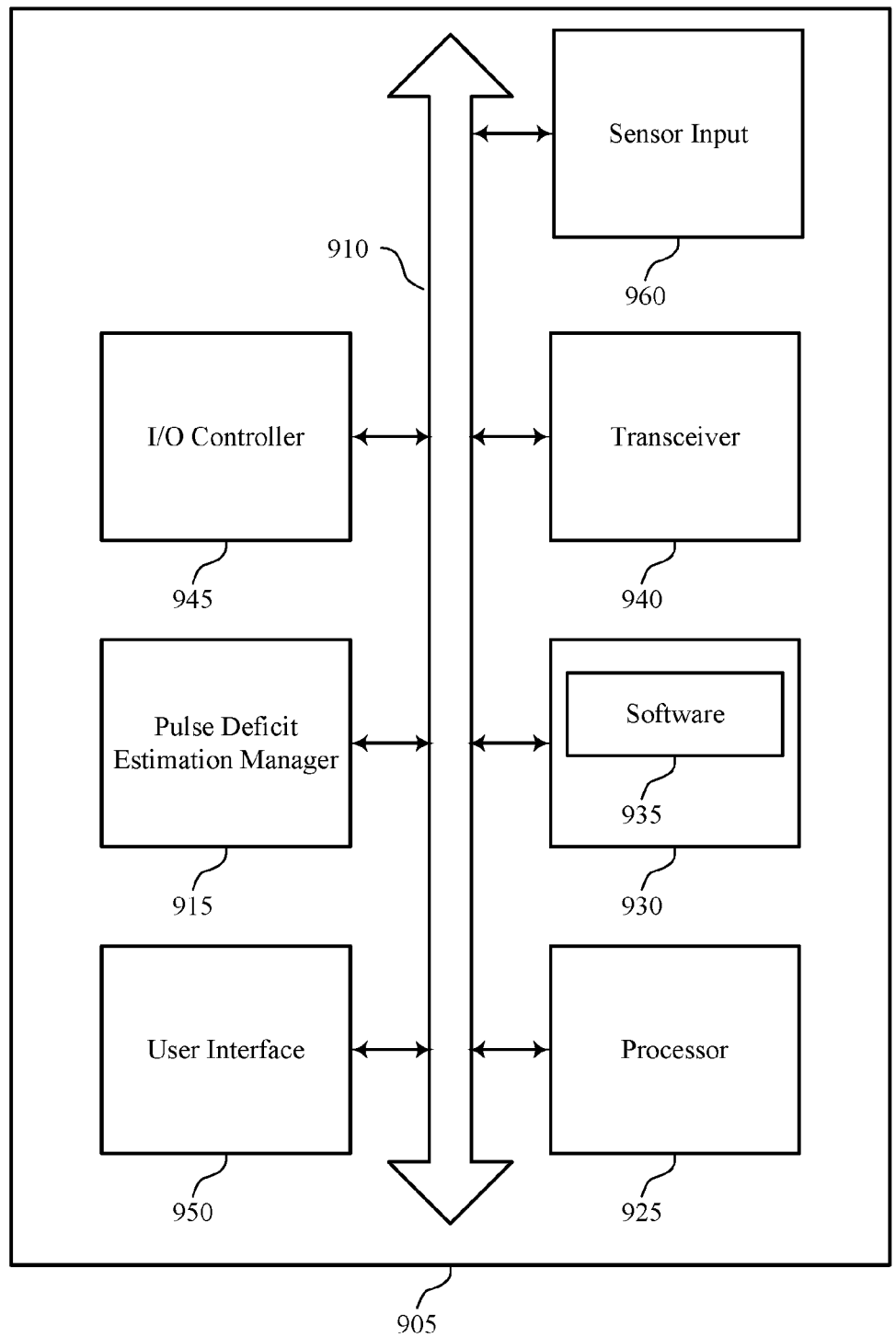
FIG. 9 illustrates a block diagram of a system including a device that supports automatic estimation of pulse deficit in accordance with aspects of the present disclosure.

FIG. 9 shows a diagram of a system 900 including a device 905 that supports automatic estimation of pulse deficit in accordance with various aspects of the present disclosure. Device 905 may be an example of or include the components of device 605, device 705, or a medical device 110 as described above, e.g., with reference to FIGS. 1-7.

Device 905 may include components for bi-directional voice and data communications including components for transmitting and receiving communications, including pulse deficit estimation manager 915, processor 925, memory 930, software 935, transceiver 940, I/O controller 945, and user interface 950. Device 905 may also include a sensor input 960.

Sensor input 960 may include hardware for interfacing with a physiological sensor and may, in some examples, include a physiological sensor. In some examples, sensor input 960 may interface with or include an ECG sensor, an arterial blood pressure sensor, an SpO2 sensor, or an accelerometer. Sensor input 960 may be equipped to communicate with sensors via a wired or a wireless interface.

Processor 925 may include an intelligent hardware device, (e.g., a general-purpose processor, a digital signal processor (DSP), a central processing unit (CPU), a microcontroller, an application specific integrated circuit (ASIC), a field-programmable gate array (FPGA), a programmable logic device, a discrete gate or transistor logic component, a discrete hardware component, or any combination thereof). In some cases, processor 925 may be configured to operate a memory array using a memory controller. In other cases, a memory controller may be integrated into processor 925. Processor 925 may be configured to execute computer-readable instructions stored in a memory to perform various functions (e.g., function or tasks supporting automatic estimation of pulse deficit).

Memory 930 may include random access memory (RAM) and read only memory (ROM). The memory 930 may store computer-readable, computer-executable software 935 including instructions that, when executed, cause the processor to perform various functions described herein. In some cases, the memory 930 can contain, among other things, a Basic Input-Output system (BIOS) which may control basic hardware and/or software operation such as the interaction with peripheral components or devices.

Software 935 may include code to implement aspects of the present disclosure, including code to support automatic estimation of pulse deficit. Software 935 can be stored in a non-transitory computer-readable medium such as system memory or other memory. In some cases, the software 935 may not be directly executable by the processor but may cause a computer (e.g., when compiled and executed) to perform functions described herein.

Transceiver 940 may communicate bi-directionally, via one or more antennas, wired, or wireless links as described above. For example, the transceiver 940 may represent a wireless transceiver and may communicate bi-directionally with another wireless transceiver. The transceiver 940 may also include a modem to modulate the packets and provide the modulated packets to the antennas for transmission, and to demodulate packets received from the antennas.

I/O controller 945 may manage input and output signals for device 905. In some cases, I/O controller 945 may utilize an operating system such as iOS®, ANDROID®, MS-DOS®, MS-WINDOWS®, OS/2®, UNIX®, LINUX®, or another known operating system. I/O controller 945 may interface with and control or manage sensor input 960.

User interface 950 may enable a user to interact with device 905. In some embodiments, the user interface module 950 may include an audio device, such as an external speaker system, an external display device such as a display screen, and/or an input device (e.g., remote control device interfaced with the user interface module 950 directly and/or through the I/O controller module). User interface 950 may include audio or display devices for sounding or displaying an alert condition, for example.

Figure 10:
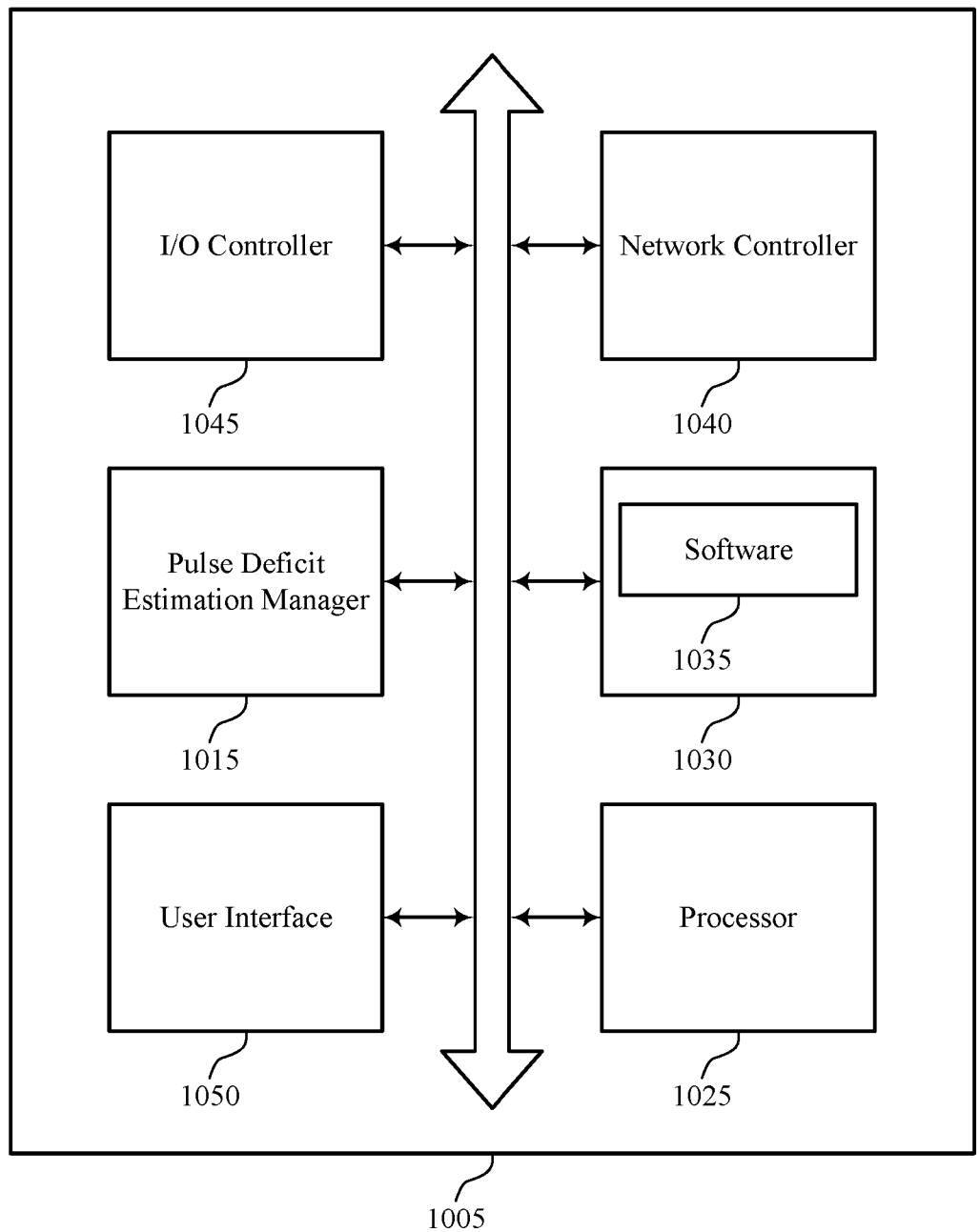
FIG. 10 illustrates a block diagram of a system including a device that supports automatic estimation of pulse deficit in accordance with aspects of the present disclosure.

FIG. 10 shows a diagram of a system 1000 including a device 1005 that supports automatic estimation of pulse deficit in accordance with various aspects of the present disclosure. Device 1005 may be an example of central station 135 as described above, e.g., with reference to FIGS. 1, 3, 4, and 5.

Device 1005 may include components for bi-directional voice and data communications including components for transmitting and receiving communications, including pulse deficit estimation manager 1015, processor 1025, memory 1030, software 1035, network controller 1040, I/O controller 1045, and user interface 1050.

Processor 1025 may include an intelligent hardware device, (e.g., a general-purpose processor, a DSP, a CPU, a microcontroller, an ASIC, a FPGA, a programmable logic device, a discrete gate or transistor logic component, a discrete hardware component, or any combination thereof). In some cases, processor 1025 may be configured to operate a memory array using a memory controller. In other cases, a memory controller may be integrated into processor 1025. Processor 1025 may be configured to execute computer-readable instructions stored in a memory to perform various functions (e.g., function or tasks supporting automatic estimation of pulse deficit).

Memory 1030 may include RAM and ROM. The memory 1030 may store computer-readable, computer-executable software 835 including instructions that, when executed, cause the processor to perform various functions described herein. In some cases, the memory 1030 can contain, among other things, a BIOS which may control basic hardware and/or software operation such as the interaction with peripheral components or devices.

Software 1035 may include code to implement aspects of the present disclosure, including code to support automatic estimation of pulse deficit. Software 1035 can be stored in a non-transitory computer-readable medium such as system memory or other memory. In some cases, the software 1035 may not be directly executable by the processor but may cause a computer (e.g., when compiled and executed) to perform functions described herein.

Network controller 1040 may communicate bi-directionally, via one or more wired or wireless links as described above. Network controller 1040 may use a variety of communications protocols to communicate with network 125. Network controller 1040 may allow device 1005 to communicate to various peripheral devices such as computing devices 115, remote databases 140, and remote computing devices 145.

I/O controller 1045 may manage input and output signals for device 1005. In some cases, I/O controller 1045 may utilize an operating system such as iOS®, ANDROID®, MS-DOS®, MS-WINDOWS®, OS/2®, UNIX®, LINUX®, or another known operating system.

User interface 1050 may enable a user to interact with device 1005. In some embodiments, the user interface module 1050 may include an audio device, such as an external speaker system, an external display device such as a display screen, and/or an input device (e.g., remote control device interfaced with the user interface module 1050 directly and/or through the I/O controller module). User interface 1050 may include audio or display devices for sounding or displaying an alert condition, for example.

Figure 11:
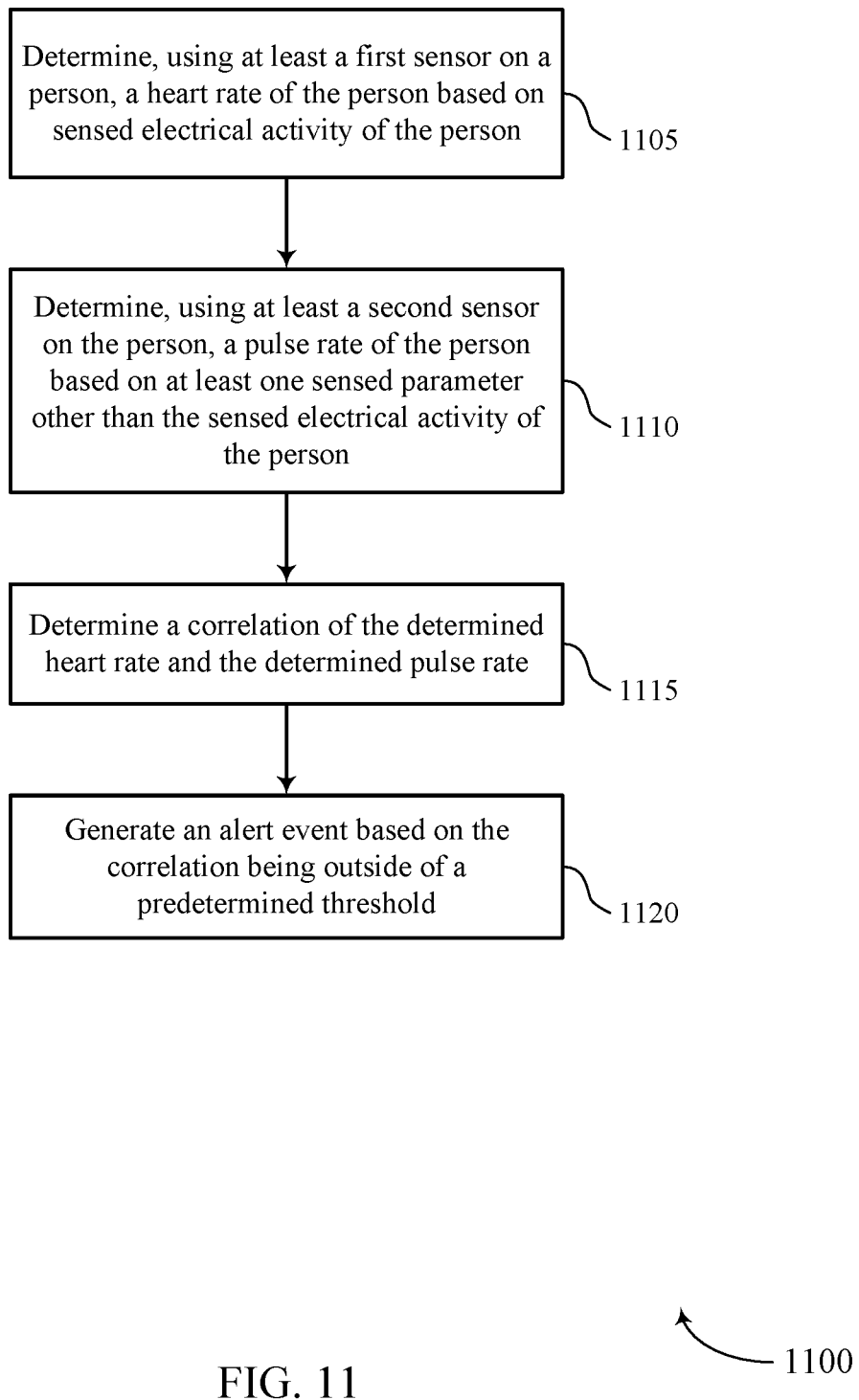
FIGS. 11 through 14 illustrate methods for automatic estimation of pulse deficit in accordance with aspects of the present disclosure.

FIG. 11 shows a flowchart illustrating a method 1100 for automatic estimation of pulse deficit in accordance with various aspects of the present disclosure. The operations of method 1100 may be implemented by a medical device 110 or its components as described herein. For example, the operations of method 1100 may be performed by a pulse deficit estimation manager as described with reference to FIGS. 6 through 8. In some examples, a medical device 110 may execute a set of codes to control the functional elements of the device to perform the functions described below. Additionally or alternatively, the medical device 110 may perform aspects of the functions described below using special-purpose hardware.

At block 1105, the medical device 110 may determine, using at least a first sensor on a person, a heart rate of the person based on sensed electrical activity of the person. The operations of block 1105 may be performed according to the methods described with reference to FIGS. 1 through 5. In certain examples, aspects of the operations of block 1105 may be performed by a heart rate module as described with reference to FIGS. 6 through 8. The sensed electrical activity may be an ECG of the person.

At block 1110, the medical device 110 may determine, using at least a second sensor on the person, a pulse rate of the person based on at least one sensed parameter other than the sensed electrical activity of the person. The operations of block 1110 may be performed according to the methods described with reference to FIGS. 1 through 5. In certain examples, aspects of the operations of block 1110 may be performed by a pulse rate module as described with reference to FIGS. 6 through 8. The sensed parameter may be an arterial blood pressure of the person, an oxygen saturation level of the person, or a pulse-related mechanical movement.

At block 1115, the medical device 110 may determine a correlation of the determined heart rate and the determined pulse rate. The operations of block 1115 may be performed according to the methods described with reference to FIGS. 1 through 5. In certain examples, aspects of the operations of block 1115 may be performed by a correlation module as described with reference to FIGS. 6 through 8. The determined correlation may comprise of comparing a timing of the determined heart rate and the determined pulse rate. The determined correlation may also comprise of comparing a frequency domain analysis of the determined heart rate and the determined pulse rate.

At block 1120, the medical device 110 may generate an alert event based on the correlation being outside of a predetermined threshold. The operations of block 1120 may be performed according to the methods described with reference to FIGS. 1 through 5. In certain examples, aspects of the operations of block 1120 may be performed by an alert module as described with reference to FIGS. 6 through 8. The alert may be transmitted to a central station 135 via a network. The alert may be stored for later transmission if the network is not available for transmission. The determined heart rate and the determined pulse rate may be transmitted with the alert event.

Figure 12:
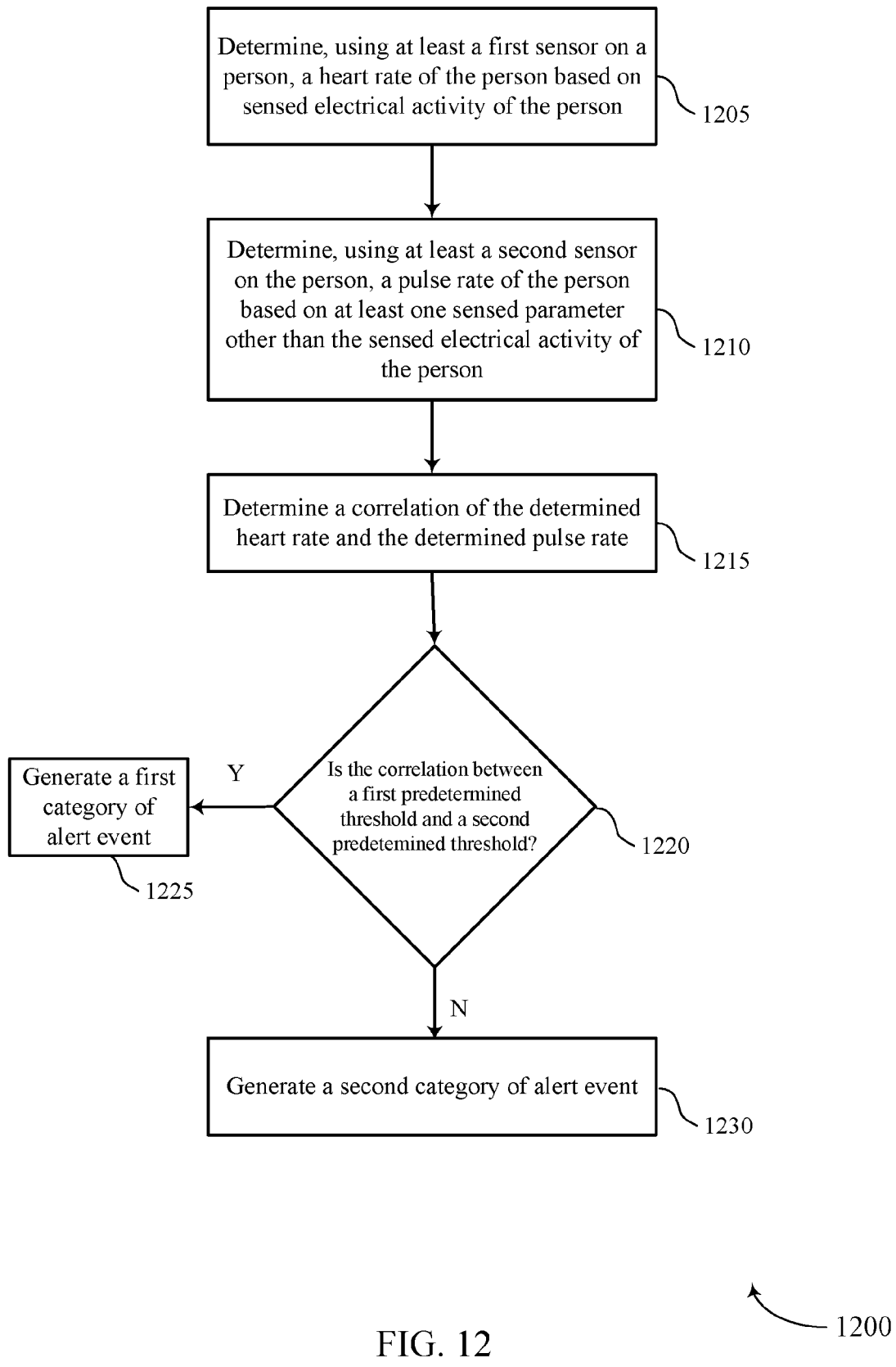

FIG. 12 shows a flowchart illustrating a method 1200 for automatic estimation of pulse deficit in accordance with various aspects of the present disclosure. The operations of method 1200 may be implemented by a medical device 110 or its components as described herein. For example, the operations of method 1200 may be performed by a pulse deficit estimation manager as described with reference to FIGS. 6 through 8. In some examples, a medical device 110 may execute a set of codes to control the functional elements of the device to perform the functions described below. Additionally or alternatively, the medical device 110 may perform aspects of the functions described below using special-purpose hardware.

At block 1205, the medical device 110 may determine, using at least a first sensor on a person, a heart rate of the person based on sensed electrical activity of the person. The operations of block 1205 may be performed according to the methods described with reference to FIGS. 1 through 5. In certain examples, aspects of the operations of block 1205 may be performed by a heart rate module as described with reference to FIGS. 6 through 8. The sensed electrical activity may be an ECG of the person.

At block 1210, the medical device 110 may determine, using at least a second sensor on the person, a pulse rate of the person based on at least one sensed parameter other than the sensed electrical activity of the person. The operations of block 1210 may be performed according to the methods described with reference to FIGS. 1 through 5. In certain examples, aspects of the operations of block 1210 may be performed by a pulse rate module as described with reference to FIGS. 6 through 8. The sensed parameter may be an arterial blood pressure of the person, an oxygen saturation level of the person, or a pulse-related mechanical movement.

At block 1215, the medical device 110 may determine a correlation of the determined heart rate and the determined pulse rate by comparing a timing of the determined heart rate and the determined pulse rate. The operations of block 1215 may be performed according to the methods described with reference to FIGS. 1 through 5. In certain examples, aspects of the operations of block 1215 may be performed by a correlation module as described with reference to FIGS. 6 through 8. The determined correlation may comprise of comparing a timing of the determined heart rate and the determined pulse rate. The determined correlation may also comprise of comparing a frequency domain analysis of the determined heart rate and the determined pulse rate.

At decision block 1220, the medical device 110 may determine whether the correlation is within a first predetermined threshold and a second predetermined threshold. If the correlation resides within the two predetermined thresholds, method 1200 proceeds to block 1225 where a first category of alert event is generated. Otherwise, method 1200 proceeds to block 1230 where a second category of alert event is generated based on the correlation falling outside of the two predetermined thresholds. The operations of decision block 1220 may be performed according to the methods described with reference to FIGS. 1 through 5. In certain examples, aspects of the operations of decision block 1220 may be performed by an alert threshold module 845 as described with reference to FIG. 8. The alerts may be transmitted to a central station 135 via a network. The alerts may be stored for later transmission if the network is not available for transmission. The determined heart rate and the determined pulse rate may be transmitted with the alert events.

Figure 13:
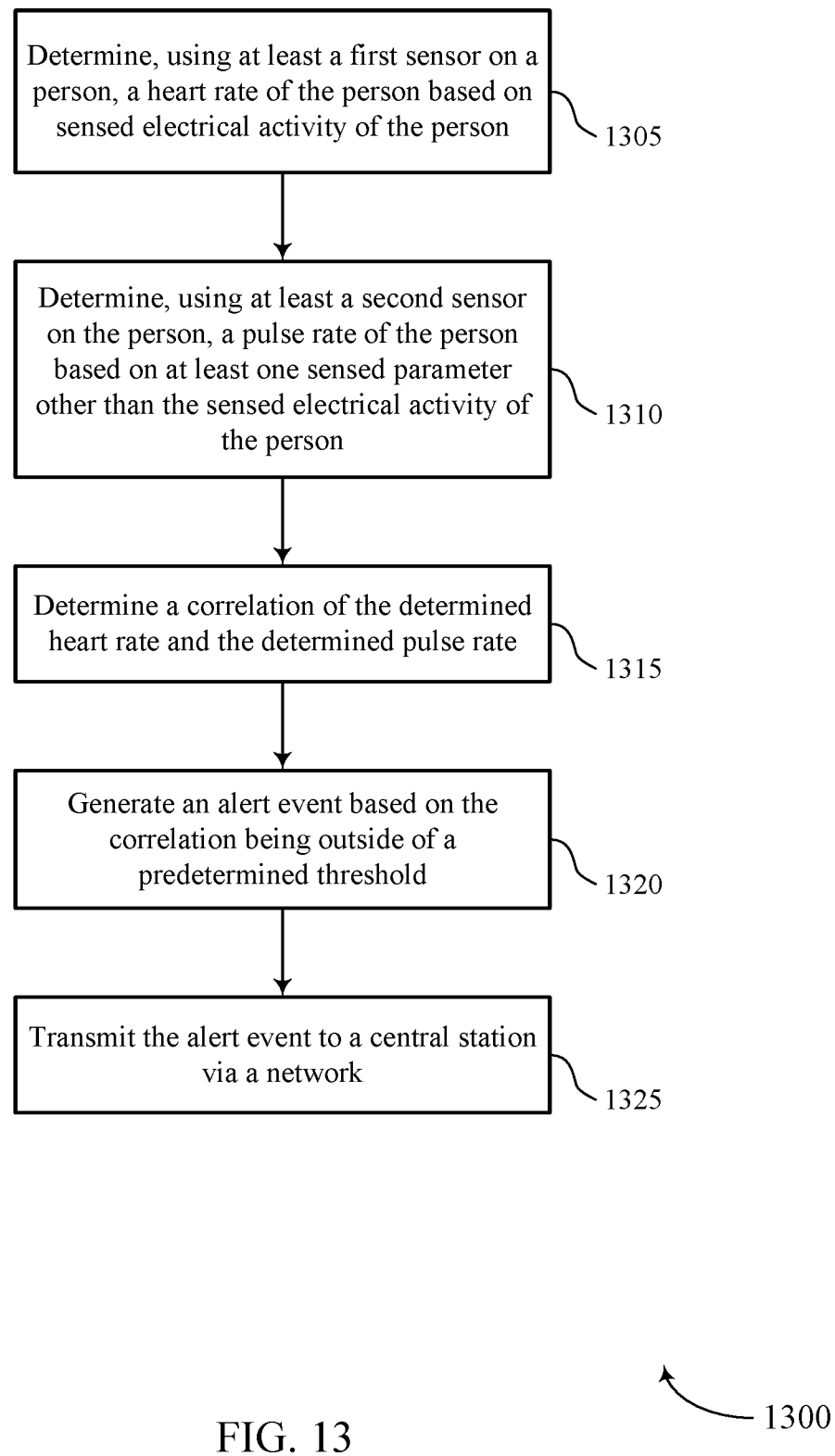

FIG. 13 shows a flowchart illustrating a method 1300 for automatic estimation of pulse deficit in accordance with various aspects of the present disclosure. The operations of method 1300 may be implemented by a medical device 110 or its components as described herein. For example, the operations of method 1300 may be performed by a pulse deficit estimation manager as described with reference to FIGS. 6 through 8. In some examples, a medical device 110 may execute a set of codes to control the functional elements of the device to perform the functions described below. Additionally or alternatively, the medical device 110 may perform aspects of the functions described below using special-purpose hardware.

At block 1305, the medical device 110 may determine, using at least a first sensor on a person, a heart rate of the person based on sensed electrical activity of the person. The operations of block 1305 may be performed according to the methods described with reference to FIGS. 1 through 5. In certain examples, aspects of the operations of block 1305 may be performed by a heart rate module as described with reference to FIGS. 6 through 8. The sensed electrical activity may be an ECG of the person.

At block 1310, the medical device 110 may determine, using at least a second sensor on the person, a pulse rate of the person based on at least one sensed parameter other than the sensed electrical activity of the person. The operations of block 1310 may be performed according to the methods described with reference to FIGS. 1 through 5. In certain examples, aspects of the operations of block 1310 may be performed by a pulse rate module as described with reference to FIGS. 6 through 8. The sensed parameter may be an arterial blood pressure of the person, an oxygen saturation level of the person, or a pulse-related mechanical movement.

At block 1315, the medical device 110 may determine a correlation of the determined heart rate and the determined pulse rate. The operations of block 1315 may be performed according to the methods described with reference to FIGS. 1 through 5. In certain examples, aspects of the operations of block 1315 may be performed by a correlation module as described with reference to FIGS. 6 through 8. The determined correlation may comprise of comparing a timing of the determined heart rate and the determined pulse rate. The determined correlation may also comprise of comparing a frequency domain analysis of the determined heart rate and the determined pulse rate.

At block 1320, the medical device 110 may generate an alert event based on the correlation being outside of a predetermined threshold. The operations of block 1320 may be performed according to the methods described with reference to FIGS. 1 through 5. In certain examples, aspects of the operations of block 1320 may be performed by an alert module as described with reference to FIGS. 6 through 8. The alert may be stored for later transmission if the network is not available for transmission. The determined heart rate and the determined pulse rate may be transmitted with the alert event.

At block 1325, the medical device 110 may transmit the alert event to a central station 135 via a network. The operations of block 1325 may be performed according to the methods described with reference to FIGS. 1 through 5. In certain examples, aspects of the operations of block 1325 may be performed by an alert module as described with reference to FIGS. 6 through 8.

Figure 14:
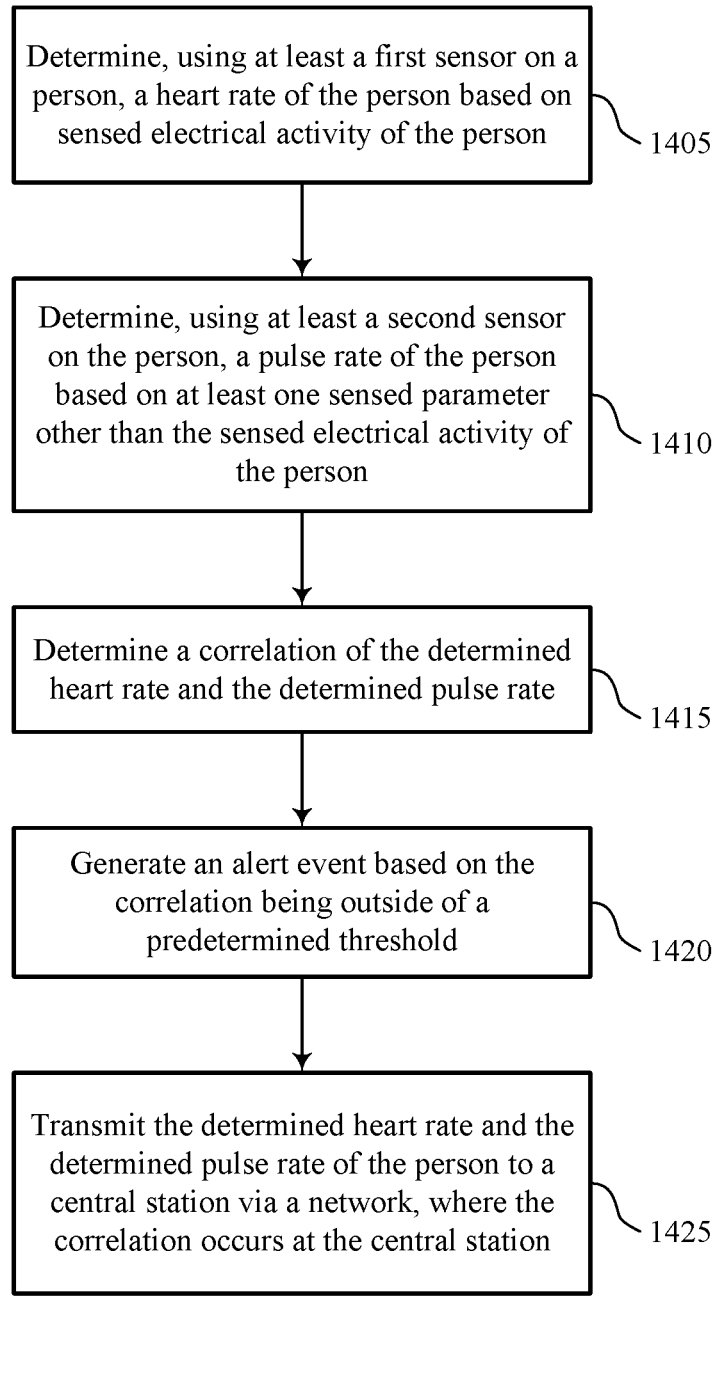

FIG. 14 shows a flowchart illustrating a method 1400 for automatic estimation of pulse deficit in accordance with various aspects of the present disclosure. The operations of method 1400 may be implemented by a medical device 110 or its components as described herein. For example, the operations of method 1400 may be performed by a pulse deficit estimation manager as described with reference to FIGS. 6 through 8. In some examples, a medical device 110 may execute a set of codes to control the functional elements of the device to perform the functions described below. Additionally or alternatively, the medical device 110 may perform aspects of the functions described below using special-purpose hardware.

At block 1405, the medical device 110 may determine, using at least a first sensor on a person, a heart rate of the person based on sensed electrical activity of the person. The operations of block 1405 may be performed according to the methods described with reference to FIGS. 1 through 5. In certain examples, aspects of the operations of block 1405 may be performed by a heart rate module as described with reference to FIGS. 6 through 8. The sensed electrical activity may be an ECG of the person.

At block 1410, the medical device 110 may determine, using at least a second sensor on the person, a pulse rate of the person based on at least one sensed parameter other than the sensed electrical activity of the person. The operations of block 1410 may be performed according to the methods described with reference to FIGS. 1 through 5. In certain examples, aspects of the operations of block 1410 may be performed by a pulse rate module as described with reference to FIGS. 6 through 8. The sensed parameter may be an arterial blood pressure of the person, an oxygen saturation level of the person, or a pulse-related mechanical movement.

At block 1415, the medical device 110 may determine a correlation of the determined heart rate and the determined pulse rate. The operations of block 1415 may be performed according to the methods described with reference to FIGS. 1 through 5. In certain examples, aspects of the operations of block 1415 may be performed by a correlation module as described with reference to FIGS. 6 through 8. The determined correlation may comprise of comparing a timing of the determined heart rate and the determined pulse rate. The determined correlation may also comprise of comparing a frequency domain analysis of the determined heart rate and the determined pulse rate.

At block 1420, the medical device 110 may generate an alert event based on the correlation being outside of a predetermined threshold. The operations of block 1420 may be performed according to the methods described with reference to FIGS. 1 through 5. In certain examples, aspects of the operations of block 1420 may be performed by an alert module as described with reference to FIGS. 6 through 8. The alert may be transmitted to a central station 135 via a network. The alert may be stored for later transmission if the network is not available for transmission. The determined heart rate and the determined pulse rate may be transmitted with the alert event.

At block 1425, the medical device 110 may transmit the determined heart rate and the determined pulse rate of the person to a central station via a network, where the correlation occurs at the central station. The operations of block 1425 may be performed according to the methods described with reference to FIGS. 1 through 5. In certain examples, aspects of the operations of block 1425 may be performed by a communication module as described with reference to FIGS. 6 through 8.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, an field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C).

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for determining a heart rate, comprising:
   detecting, using at least a first sensor on a person, a heart rate of the person based on sensed electrical activity of the person;
   detecting, using at least a second sensor on the person, a pulse rate of the person based on at least one sensed parameter other than the sensed electrical activity of the person;
   transmitting, from the first sensor to the second sensor, the detected heart rate of the person;
   comparing, at the second sensor, a frequency domain analysis of the determined heart rate and the determined pulse rate; and
   generating, at the second sensor, an alert event based at least in part on a measure associated with the comparison being outside of a predetermined threshold.

2. The method of claim 1, further comprising:
   comparing a timing of the determined heart rate and the determined pulse rate.

3. The method of claim 1, wherein
   the alert event indicates a Pulseless Electrical Activity (PEA) condition.

4. The method of claim 1, wherein
   the sensed electrical activity of the person is an electrocardiogram (ECG) of the person.

5. The method of claim 1, wherein
   the at least one sensed parameter is based on an arterial blood pressure of the person.

6. The method of claim 1, wherein
   the predetermined threshold is comprised of a first predetermined threshold and a second predetermined threshold; and
   generating the alert event comprises: generating a first category of alert event when the measure is between the first predetermined threshold and the second predetermined threshold, and generating a second category of alert event when the measure is outside of both the first predetermined threshold and the second predetermined threshold.

7. The method of claim 1, further comprising:
   determining the measure over a period of time where multiple periods of the person's heart rate and pulse rate are determined.

8. The method of claim 1, further comprising:
   remotely updating the predetermined threshold.

9. The method of claim 1, further comprising:
   transmitting the alert event to a central station via a network.

10. The method of claim 9, further comprising:
    storing the alert event for later transmission if the network is not available for transmission.

11. The method of claim 9, further comprising:
    transmitting, with the alert event, the determined heart rate and the determined pulse rate.

12. The method of claim 1, wherein
    determining the pulse rate comprises: obtaining a sensed parameter via an accelerometer, oximeter, or an optical pulse rate monitor.

13. An apparatus for determining a heart rate, the apparatus comprising:
    a processor;
    an alert module configured to generate an alert event; and
    memory in electronic communication with the processor, wherein
    the memory is configured to store instructions and the processor is configured to execute the instructions to cause the processor to:
    detect, using at least a first sensor on a person, a heart rate of the person based on sensed electrical activity of the person;

detect, using at least a second sensor on the person, a pulse rate of the person based on at least one sensed parameter other than the sensed electrical activity of the person;

transmit, from the first sensor to the second sensor, the detected heart rate of the person; and compare, at the second sensor, a frequency domain analysis of the determined heart rate and the determined pulse rate, wherein the alert module is configured to generate, at the second sensor, the alert event based at least in part on a measure associated with the comparison being outside of a predetermined threshold.

14. The apparatus of claim 13, wherein the memory configured to store the instructions and the processor configured to execute the instructions are further configured to cause the processor to:

compare a timing of the determined heart rate and the determined pulse rate.

15. The apparatus of claim 13, wherein
the alert event indicates a Pulseless Electrical Activity (PEA) condition.

16. An apparatus for determining a heart rate, comprising:

means for detecting, using at least a first sensor on a person, a heart rate of the person based on sensed electrical activity of the person;

means for detecting, using at least a second sensor on the person, a pulse rate of the person based on at least one sensed parameter other than the sensed electrical activity of the person;

means for transmitting, from the first sensor to the second sensor, the detected heart rate of the person;

means for comparing, at the second sensor, a frequency domain analysis of the determined heart rate and the determined pulse rate; and means for generating, at the second sensor, an alert event based at least in part on a measure associated with the comparison being outside of a predetermined threshold.

* * * * *